United States Patent
Purcell

(10) Patent No.: US 7,481,813 B1
(45) Date of Patent: Jan. 27, 2009

(54) SECURING DEVICE AND CORRESPONDING METHODS THEREOF FOR BONE FIXATION SYSTEMS

(75) Inventor: Thomas Purcell, Del Mar, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 123 days.

(21) Appl. No.: 11/284,727

(22) Filed: Nov. 21, 2005

Related U.S. Application Data

(60) Provisional application No. 60/629,444, filed on Nov. 19, 2004.

(51) Int. Cl.
    *A61F 5/00* (2006.01)
(52) U.S. Cl. .................................. 606/86 R; 606/86 A
(58) Field of Classification Search .................. 606/86, 606/99, 104, 90, 61, 72, 86 R, 86 A
    See application file for complete search history.

(56) References Cited

U.S. PATENT DOCUMENTS

| | | | |
|---|---|---|---|
| 5,720,751 A * | 2/1998 | Jackson ........................ | 606/86 |
| 5,910,141 A * | 6/1999 | Morrison et al. .............. | 606/61 |
| 5,935,133 A * | 8/1999 | Wagner et al. ............... | 606/103 |
| 6,113,605 A * | 9/2000 | Storer .......................... | 606/99 |
| 6,440,133 B1 * | 8/2002 | Beale et al. ................... | 606/61 |
| 6,599,295 B1 * | 7/2003 | Tornier et al. ............... | 606/104 |
| 6,648,888 B1 * | 11/2003 | Shluzas ....................... | 606/61 |
| 7,179,261 B2 * | 2/2007 | Sicvol et al. .................. | 606/73 |

* cited by examiner

Primary Examiner—Pedro Philogene
(74) Attorney, Agent, or Firm—Mintz, Levin, Cohn, Ferris, Glovsky and Popeo

(57) ABSTRACT

Embodiments of the present invention are directed to devices, systems and associated methods for use in rod reduction and set screw insertion for a bone/spinal fixation system. In one embodiment of the invention, a device is provided for rod-reduction and set-screw insertion and may include a housing, a barrel provided with the housing and defining bifurcated end portions, an outer drive shaft slidably mounted on the barrel, a collar carried by the outer drive shaft for drawing the end portions of the barrel together as the collar is moved thereover, an inner drive shaft slidably and rotatably mounted within the outer drive shaft, a handle disposed at a an end of the outer drive shaft for effecting slidable and/or rotatable movement of at least one of the outer and inner drive shafts, a screw drive carried by the forward end of the inner drive shaft for engaging a set screw, a first lever actuated means for moving the outer drive shaft forwardly through the barrel in response to the squeezing of the first lever and a second lever for actuating a release mechanism for selectively allowing rearward movement of the outer drive shaft.

20 Claims, 9 Drawing Sheets

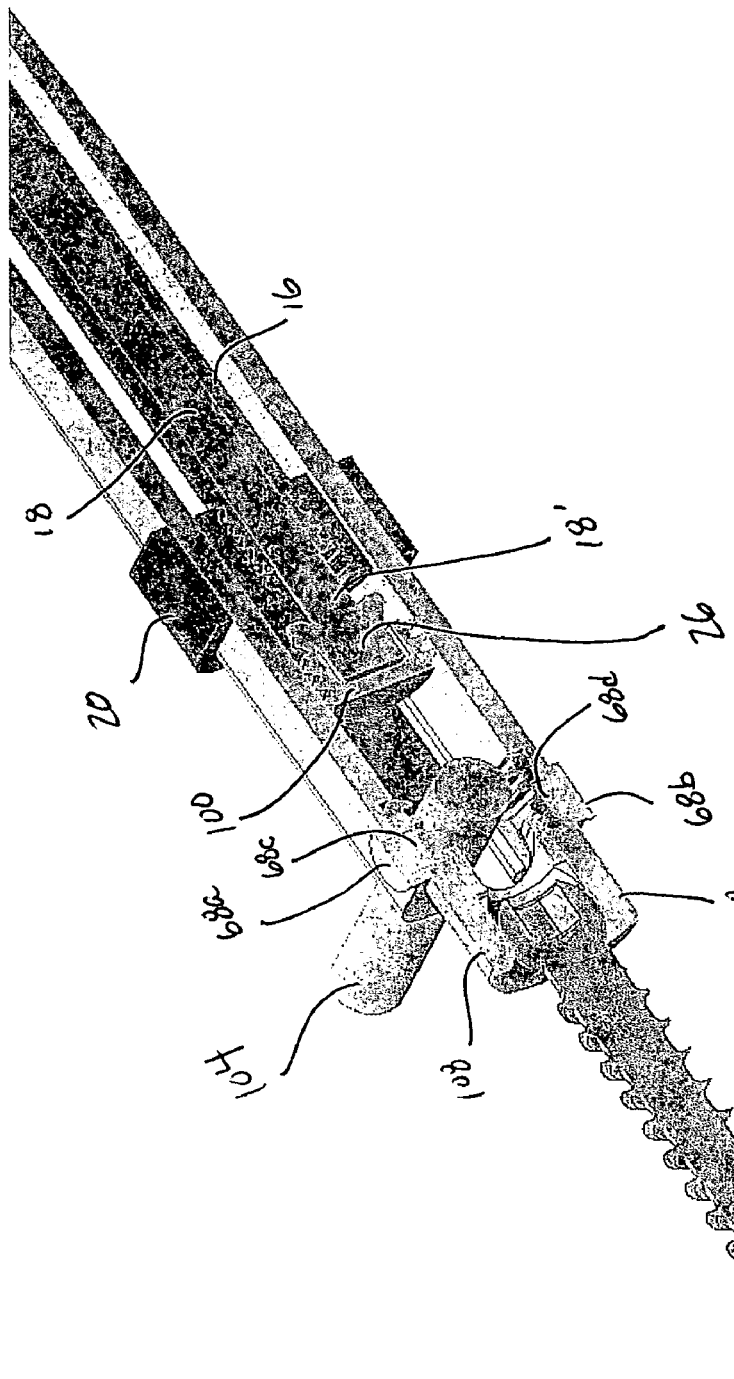

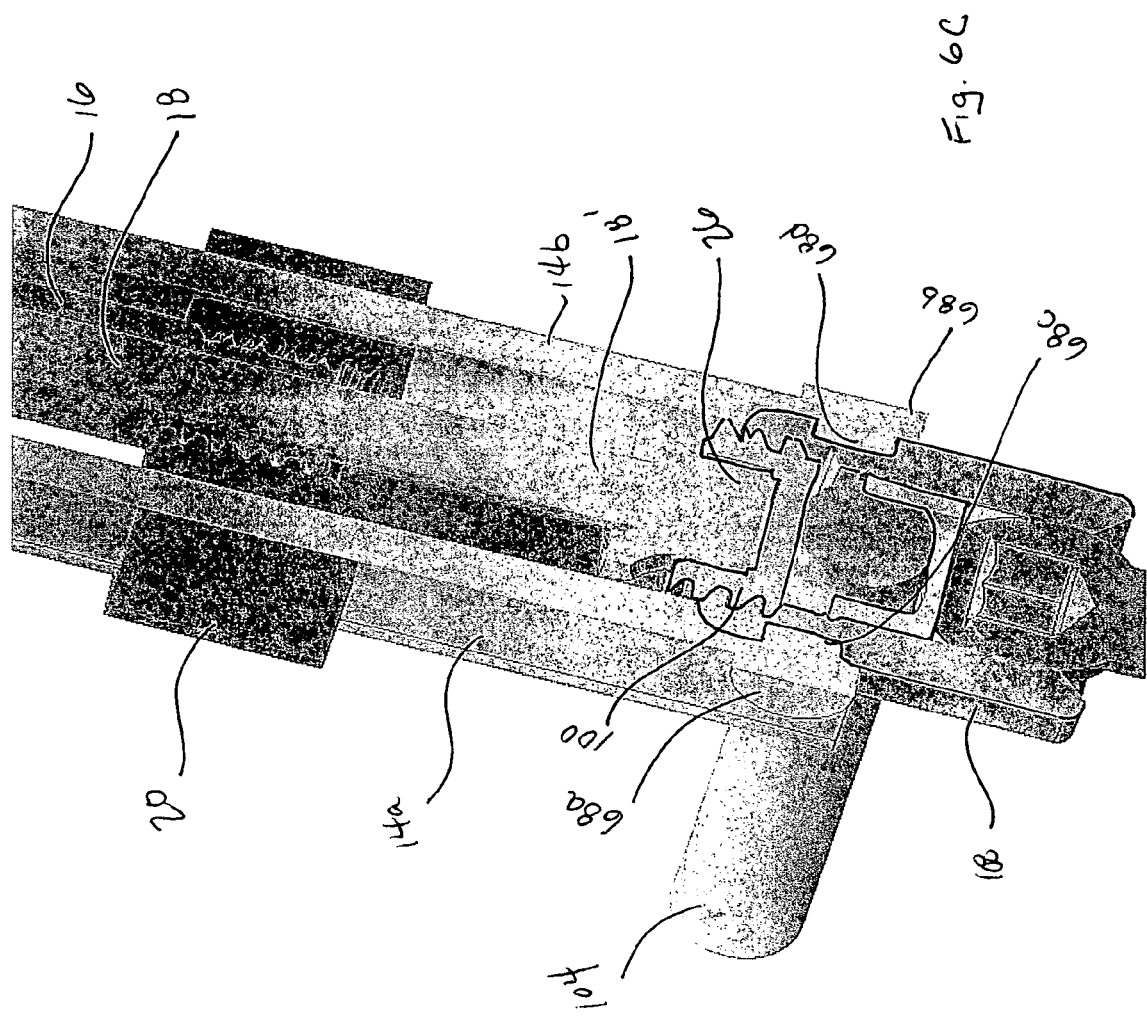

SECURING DEVICE AND CORRESPONDING METHODS THEREOF FOR BONE FIXATION SYSTEMS

CLAIM TO PRIORITY AND CROSS-REFERENCED DOCUMENTS

The subject application claims priority under 35 U.S.C. §119(e) to U.S. provisional patent application No. 60/629,444, filed Nov. 19, 2004, and is related to co-pending patent application Ser. No. 10/848,946, filed May 19, 2004, entitled, "Variable Angle Spinal Screw Assembly". Each of the foregoing disclosures are incorporated herein in their entirety by reference.

FIELD OF THE INVENTION

Embodiments of the present invention are directed to methods and devices for the installation of spinal fixation systems, and more particularly to a multipurpose driving device for use in inter-operational procedures involving the implantation of spinal fixation systems.

BACKGROUND OF THE INVENTION

Spinal fixation systems typically require the threaded securement of some form of bone anchor and the like or bone screw-assembly into two or more vertebrae, as well as the which requires the drawing of the rod to the anchors/screw-assemblies, or drawing the anchors/screw-assemblies to the rod.

Typically, these procedures are performed by a surgeon using separate tools. By way of example, Applicant has previously developed a new variable angle spinal screw-assembly that provides adjustable securement of a stabilization rod between at least two vertebrae to effect internal fixation of the spine across those vertebrae (co-pending U.S. patent application Ser. No. 10/848,946, filed May 19, 2004, the entire disclosure herein incorporated by reference). As indicated above, this spinal screw-assembly is used with at least one other such assembly to secure a stabilization rod and includes a pedicle screw, a body member and a locking cap. The pedicle screw may include a substantially spherical or elliptical head portion defining a slot therein used to drive the threaded shaft portion of the screw into a vertebrae. The body member of the screw assembly is generally cylindrical in configuration and adapted to receive the head portion of the pedicle screw and cooperate therewith so as to define a modified ball-joint. This design allows for variable angular movement of the body member with respect to the pedicle screw with the threaded shaft portion of the screw extending through an opening in the end of the body member.

The body member additionally preferably defines a pair of opposed parallel slots (or a single slot or receiving an end of a rod) axially disposed in the side wall thereof forming a saddle to receive a portion of the cylindrical fixation rod. A set screw is used to threadably engages the body member of the screw assembly to secure the stabilizing rod within the body member.

A screw driver may be used to tighten the set screw, while a separate tool is necessary to either draw the fixation rod down into the opposed slots in the body member of the screw assembly or, when necessary, to draw the pedicle screw and attached vertebrae outwardly to the rod to effect the desired alignment of the vertebrae and the securement of the rod.

SUMMARY OF THE INVENTION

Accordingly, embodiments of the present invention present a device (tool) for drawing together a spinal fixation rod with a bone anchor/screw-assembly. In some embodiments, a bone anchor/screw assembly preferably means any nail, rod, frictional fit or screw type fastener, which is received into bone, with or without bone cement, which includes a head or body member portion (which may be a separate piece from the actual anchor portion, or integral therewith) having portions thereof for receiving a rod. Some embodiments of the present invention obviate the need for separate tools and for the surgeon to repeatedly replace one tool for another to affix bone stabilization rods to bone anchors. It is worth noting, that "forwardly" or "forward" relate to a direction as indicated by arrow A in FIG. 1, and "rearwardly" or "rear" relate to an opposite direction as indicated by arrow B in FIG. 1.

Briefly, some of the embodiments of the present invention include a handheld and operated device for use in rod reduction and set-screw insertion, tightening and adjustment in connection with the implantation of spinal fixation systems of the type employing screw assembly anchors and fixation rods.

In some embodiments of the invention, the device comprises a bifurcated barrel portion, an elongated outer drive shaft slidably mounted within the barrel portion and an elongated inner drive shaft slidably and rotatably disposed within the outer drive shaft. The inner drive shaft preferably includes a T-shaped handle at its rearward end for effecting reciprocal and rotational movement thereof and a hex configuration at its forward or distal end for engaging a correspondingly configured slot in the head of a set screw.

The outer drive shaft according to some embodiments may be provided with a collar at its extended end that fits about the bifurcated barrel portion and urges the two barrel portions inwardly as it passes thereover so as to enable the extended ends of the barrel to grip a workpiece (e.g., body member of a bone/pedicle screw assembly). A pair of laterally spaced parallel pusher bars may extend forwardly of the collar and define abutment surfaces at their extended ends for engaging a fixation rod. While some preferred embodiments include a pair of parallel pusher bars, the present invention may use a single pusher bar. In an embodiment utilizing a pair of pusher bars, the laterally spacing of the bars also allows the hexagonally configured end of the inner drive shaft to pass therebetween.

A pistol grip type handle may be provided in some embodiments for conveniently holding the device such that the forward or extended ends of the barrel and drive shafts are adjacent the workpiece. The device may also include a pivotally mounted first lever and associated spring-biased camber lock for incrementally advancing the outer drive shaft forwardly with each successive actuation/squeezing of the first lever and a spring-biased second release lever and associated camber lock for allowing the outer drive shaft to move rearwardly in response to the squeezing of the release lever.

In the implantation of a bone or spinal fixation system according to some embodiments of the invention, the screw handling/rod reduction device of the present invention may first be loaded with a set screw by pushing the handle at the rear of the inner drive shaft forwardly such that the hexagonal driver at the extended or distal end of the shaft protrudes through the pusher rods at the distal end of the outer drive shaft and forwardly of the bifurcated barrel portion of the device. While holding the handle in the forward position, the hexagonal end of the inner drive shaft is pressed into the head of a set screw, attaching the screw to the shaft. Actuating the release/second lever while pulling rearwardly on the T-handle, pivots the camber lock associated with the release lever, allowing the outer drive shaft to be pulled rearwardly with the inner drive shaft and the attached set screw, loading the set screw in the barrel of the device.

A stabilization rod can then be disposed between the distal ends of the bifurcated barrel and positioned over a pedicle screw body member. Alignment indicators on the barrel of the device are aligned with slot in the body member so as to align the stabilization rod with the slots, and may also allow the end portions of the barrel to be removable locked onto the body member of the screw assembly. Repeated actuation of the first lever causes the spring-biased camber lock adjacent the first lever to urge the outer drive shaft forwardly. As the outer shaft moves forwardly, the planar ends of the pusher rods at the end of the shaft will abut the stabilization rod as the collar carried by the outer drive shaft causes the distal ends of the barrel to move inwardly toward each other to engage the body member. Continued actuation-squeezing of the first lever causes the camber lock to continue to move the outer drive shaft forwardly, which causes the stabilization rod to be firmly seated in the saddle of the body member.

Depending on the particular application, the outer drive shaft may either force the rod downwardly into the slots of the body member or, by virtue of the gripping engagement of the barrel portion with the body member, pull the body member, screw head and attached vertebra/bone upwardly about the rod, securing the rod and aligning the attached vertebrae with its adjacent vertebrae.

Once the stabilization rod is firmly seated in the saddle of the body member, turning the T-shaped handle at the rear of the inner drive shaft in a clockwise direction will seat the set screw carried by the forward end of the drive shaft in the body member over the transverse portion of the stabilization rod held therein. Once tension is felt, a one-quarter counterclockwise turn (for example) of the handle will relieve the tension in the locking mechanism and allow for easy removal of the device after reduction is complete. Simultaneous actuation of the release lever and withdrawal of the inner drive shaft by pulling rearwardly on the handle allows the instrument to be pulled from the body member.

Accordingly, in one embodiment of the invention, a surgical tool is provided and may include a support member having an end portion, an outer drive shaft capable of movement relative to the barrel, an inner drive shaft, a drive provided a forward end of the inner drive shaft and an actuator capable of moving the outer drive shaft in a first direction through and/or relative to the support member in response to the actuation of the actuator.

In another embodiment of the invention, a spinal fixation tool is provided and may include a housing a barrel attached to the housing and defining bifurcated end portions, an outer drive shaft slidably mounted on the barrel, a collar conveyed by the outer drive shaft for drawing the end portions of the barrel together as the collar is moved thereover, an inner drive shaft slidably and rotatably mounted within the outer drive shaft, a handle provided adjacent a rearward end of the outer drive shaft for effecting slidable and rotatable movement thereof, a screw drive provided on an end of the inner drive shaft for engaging a set screw, a first lever for moving the outer drive shaft in a first direction through the barrel in response to actuation of the first lever and a second lever for actuating a release mechanism for selectively allowing movement of the outer drive shaft in a second direction opposite to the first direction.

In yet another embodiment of the present invention, a method for securing a rod within a bone anchor may include providing a bone fixation tool according to one or more of the embodiments disclosed in the present application. Such a tool may include a housing, a barrel portion attached to the housing and defining bifurcated end portions, where at least one of the end portions includes a first mating portion for mating with a respective mating portion of a bone anchor of a bone fixation system, an outer drive shaft slidably mounted relative to the barrel, a collar attached to an end of the outer driver shaft for drawing the end portions of the barrel together as the collar is moved along the barrel in a first direction toward a distal end of the barrel, an inner drive shaft slidably and rotatably mounted within the outer drive shaft, a screw drive provided on an end of the inner drive shaft for engaging a set screw, a first actuator for moving the outer drive shaft in the first direction through the barrel in response to actuation of the first lever and a second lever for actuating a release mechanism for selectively allowing movement of the outer drive shaft in the second direction.

The above method embodiment may also include moving the inner drive shaft to a position for receiving a set screw, loading the screw drive with a set screw, actuating the second lever so as to allow movement of the inner and outer drive shaft in the second direction, substantially concurrently with actuating the second lever, moving the inner and outer drive shaft in the second direction, positioning a transverse section of a bone stabilization rod between the bifurcated end portions, positioning the mating portions of the bifurcated end portions adjacent corresponding mating portions of a bone anchor to which the bone stabilization rod will be affixed, actuating the first lever at least once so as to urge the outer drive shaft in the first direction so that a portion of the collar contacts the stabilization rod and urges the stabilization rod into a receiving portion of the bone anchor until the stabilization rod is firmly seated within the receiving portion, moving the inner drive shaft in the first direction so that the set screw is received in corresponding receiving portion on the bone anchor and rotating the inner drive shaft so as to tighten the set screw to the bone anchor.

In another embodiment of the present invention, a method for securing a rod within a bone anchor is provided and may include pushing a rod into a recess of body member of a bone anchor assembly using leverage obtained from grasping the bone anchor assembly.

While embodiments of the present invention may be used in surgical installation of implants and bone fixation (e.g., spinal fixation) devices and systems, the embodiments may also be used in any industry/profession where a rod/linear member is secured into a second member (e.g., an anchor/screw and the like).

These and other embodiments, objects and advantages of the present invention will become even more apparent with reference to the following detailed description and attached drawings. A brief description of the drawings is provided below.

BRIEF DESCRIPTION OF THE DRAWINGS

FIG. 6B is a schematic of a perspective, cross-sectional view of a distal end of the securing device according to some of the embodiments of the invention as used with a bone fixation system prior to a set screw being received.

FIG. 6C is a schematic of a perspective, cross-sectional view of a distal end of the securing device according to some of the embodiments of the invention as used with a bone fixation system after a set screw being received.

DETAILED DESCRIPTION OF THE EMBODIMENTS

Figure 1:
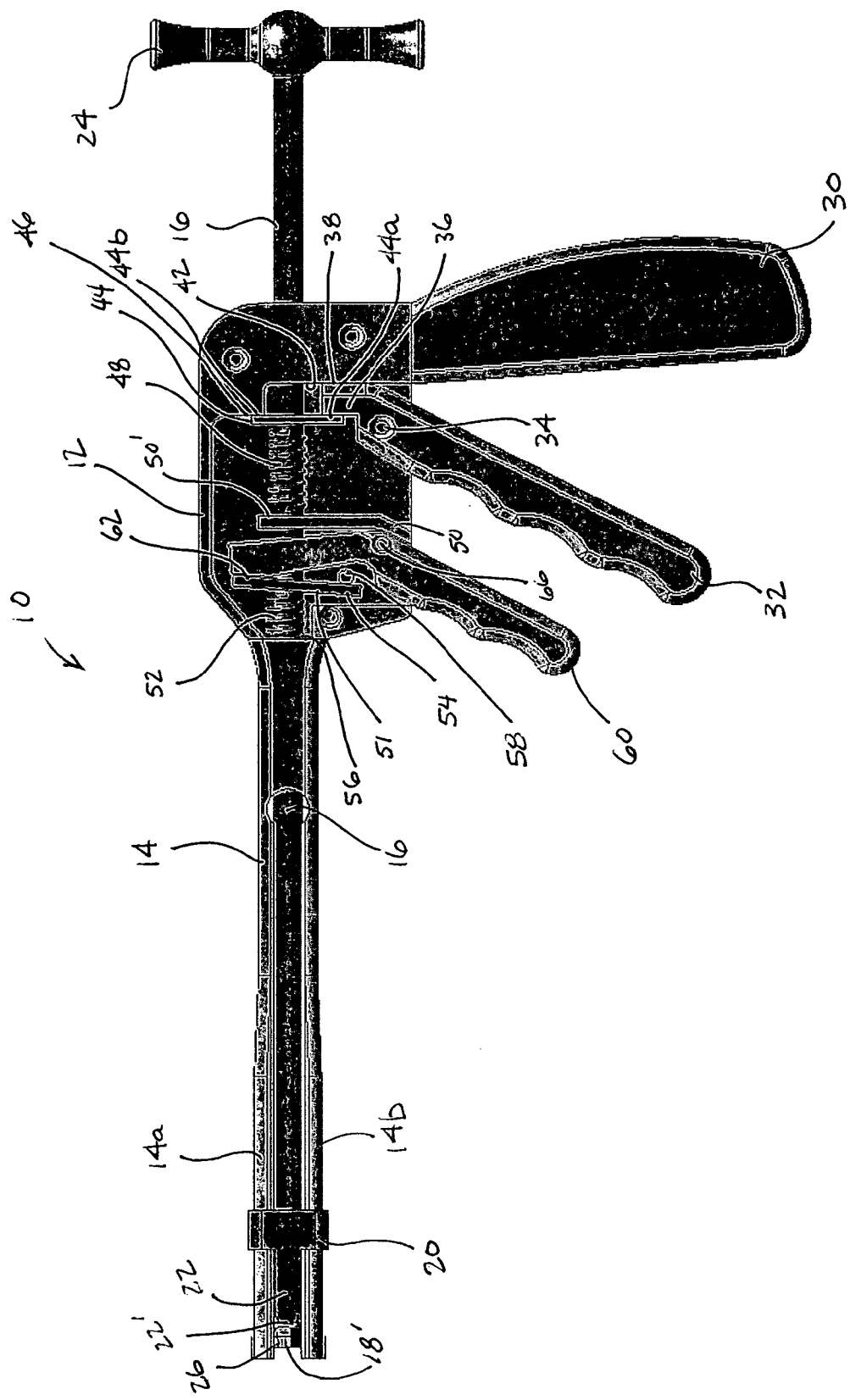
FIG. 1 is a schematic of a side view of a securing device for a bone fixation system with portions broken away to illustrate the interior of the device according to some of the embodiments of the present invention.
Figure 2:
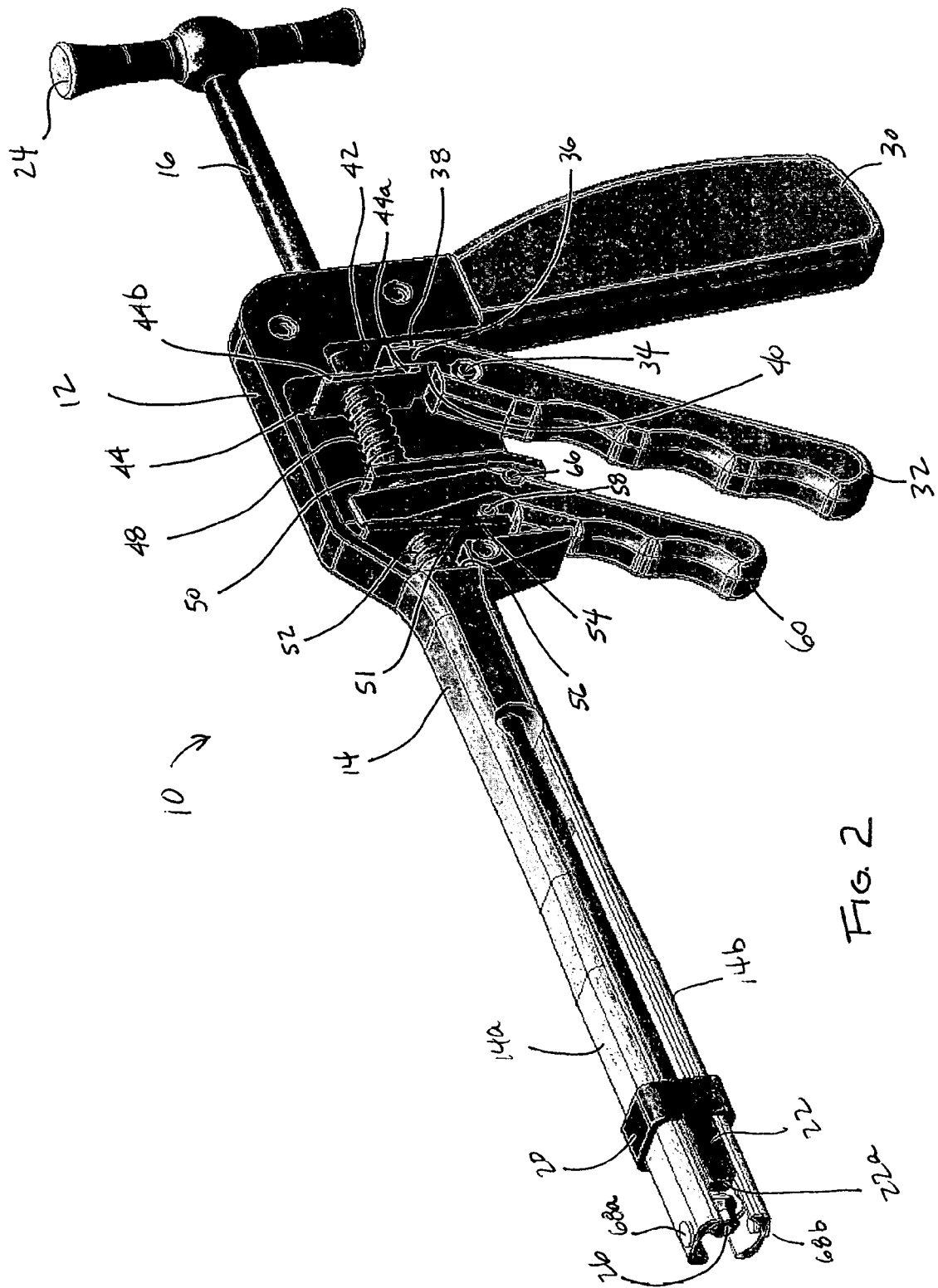
FIG. 2 is a schematic of a perspective view of the securing device according to some of the embodiments of the invention.
Figure 3:
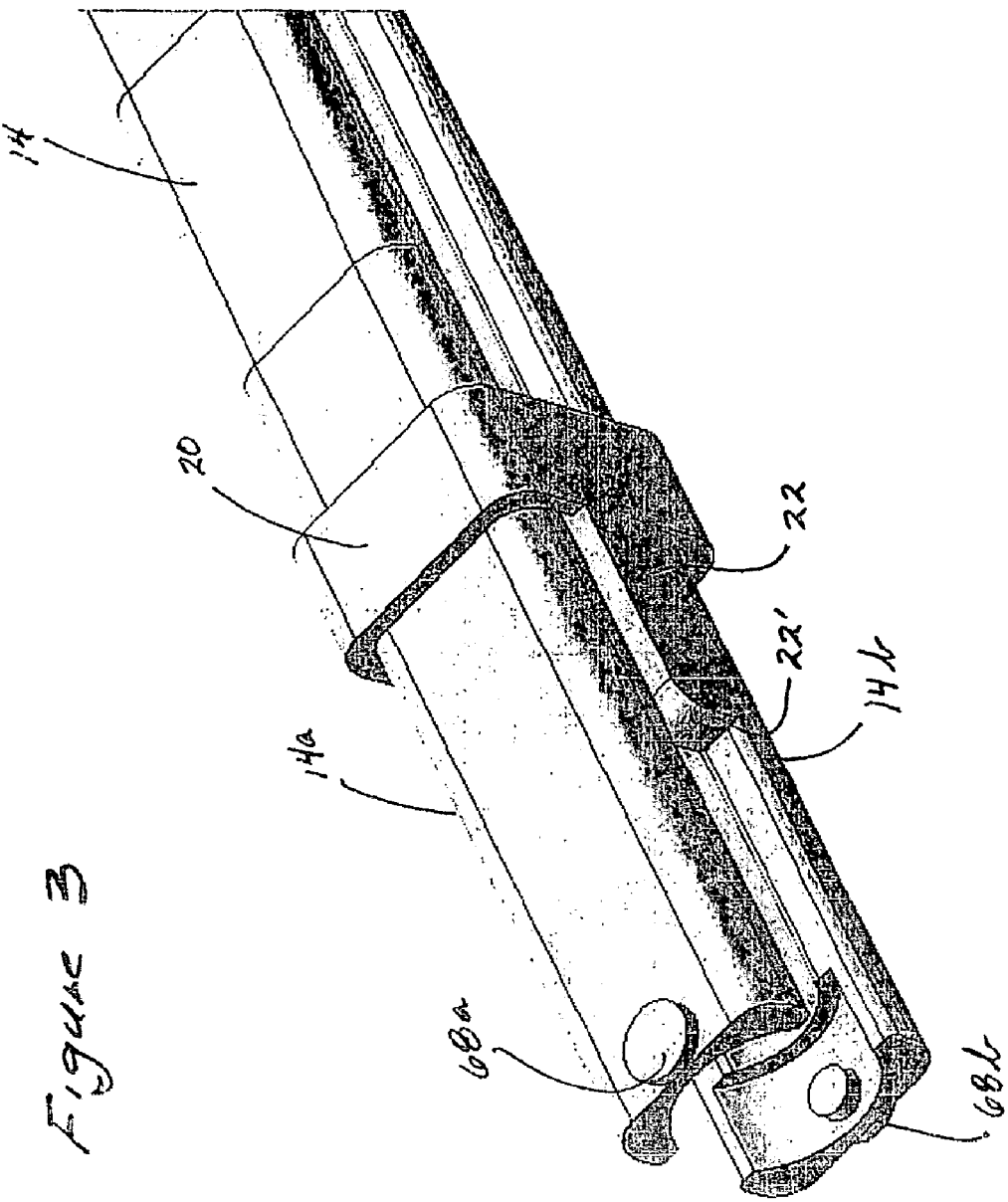
FIG. 3 is a schematic of a perspective view of a distal end of the securing device according to an embodiment of the invention.
Figure 4:
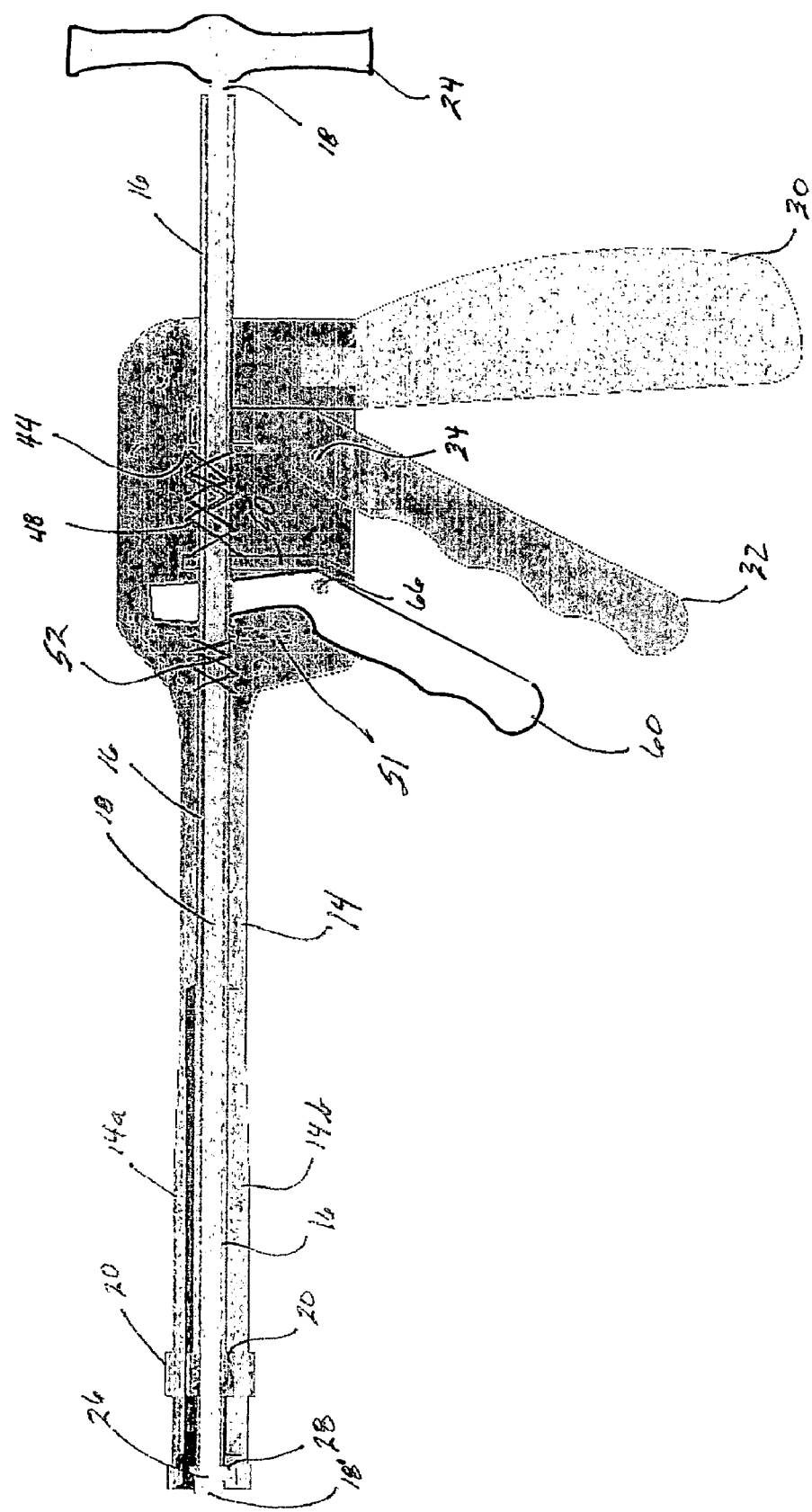
FIG. 4 is a schematic of a cross-sectional view of the securing device according to some of the embodiments of the invention.
Figure 5:
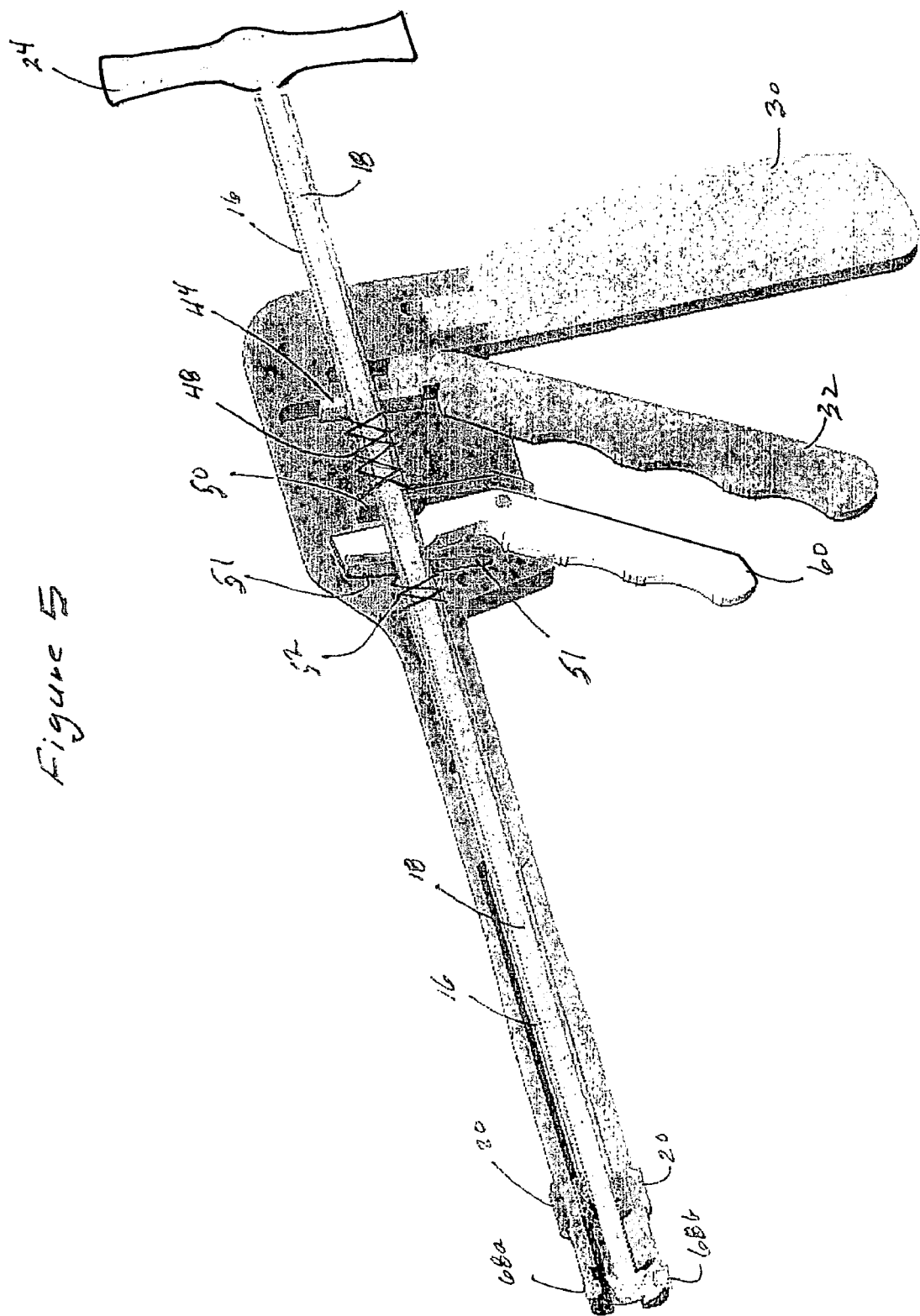
FIG. 5 is a schematic of a perspective, cross-sectional view of the securing device according to some of the embodiments of the present invention.
Figure 6A:
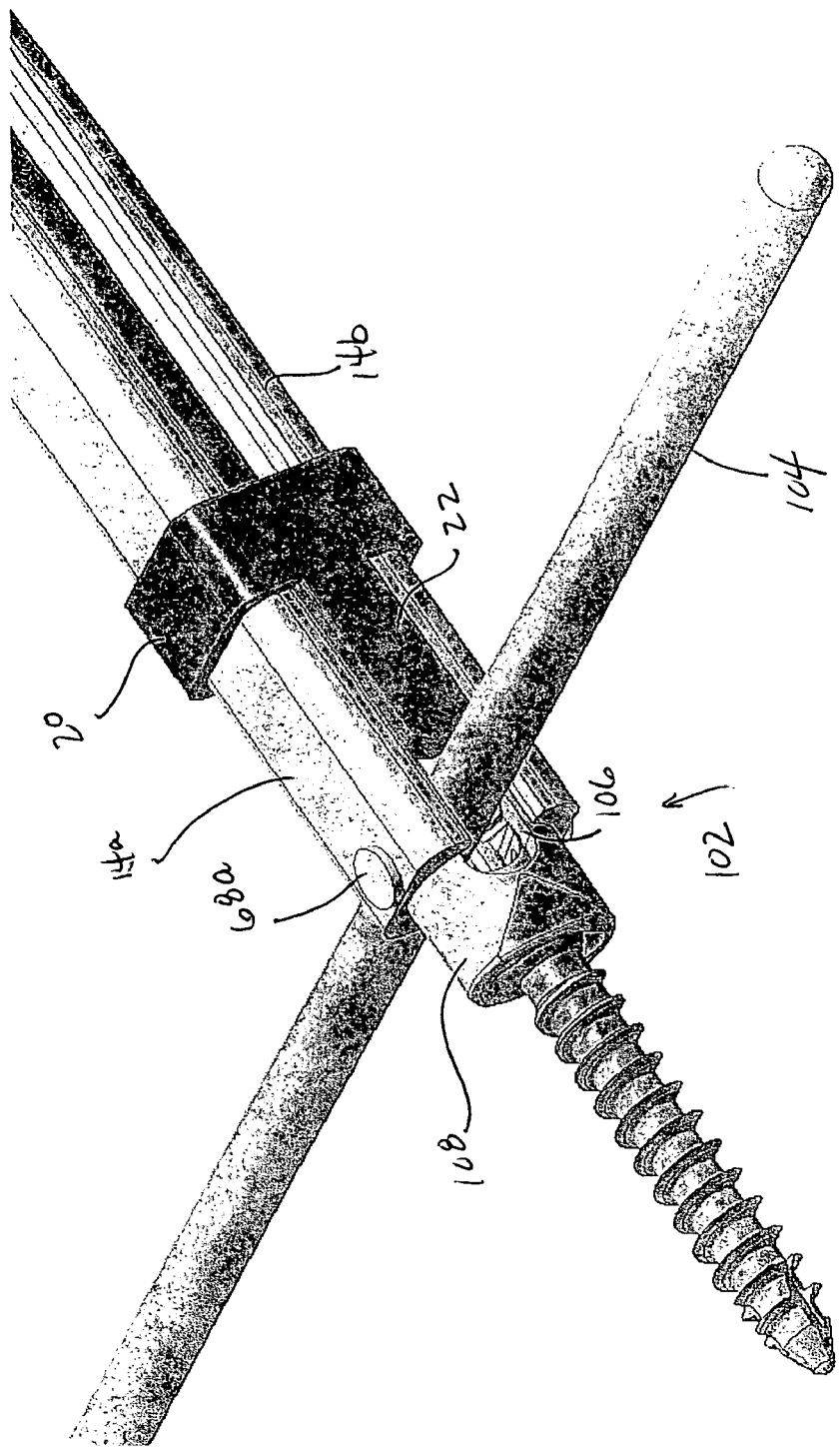
FIG. 6A is a schematic of a perspective view of a distal end of the securing device according to some of the embodiments of the invention as used with a bone fixation system.

Referring now in detail to the drawings, some embodiments of the present invention are directed to a screw handling/rod reduction device 10 (i.e., surgical tool) and may include a housing 12, a bifurcated barrel portion 14 (which may be a single support member), a cylindrical outer drive shaft 16 and a cylindrical inner drive shaft 18. The barrel portion 14 generally projects forwardly from housing 12 and may define bifurcated end portions 14a and 14b (or one support member). The housing may comprising two pieces, a base for setting the components therein, and a cover (not shown).

The cylindrical outer drive shaft 16 may be slidably mounted within the barrel portion 14 and may project rearwardly from the housing as shown in the drawings. The forward or distal end of the outer drive shaft 16 may include a member 20 (e.g., a collar) having one or preferably a pair of parallel pusher bars 22 which are preferably integrally formed therewith (or may be affixed via fastening and/or the like) and extend toward the distal end therefrom, preferably between the bifurcated portions 14a and 14b of barrel 14.

The collar 20 preferably extends about the bifurcated barrel portions 14a and 14b and is preferably sized (in some embodiments) so as to urge the two barrel portions inwardly toward each other as the collar 22 moves thereover (e.g., toward the distal end of the barrel). In a single support member embodiments, the collar may merely slide relative thereto. The pusher bars 22 may be spaced laterally apart so as to allow the forward portion of the inner drive shaft 18 to pass therebetween as will be described. The ends 22' of bars 22 are configured so as to enable the bars to push against a stabilization bar and urge the bar into the slots in a pedicle screw assembly as will also be described below. The inner drive shaft 18 may be slidably and rotatably disposed within the outer drive shaft 16 and may be provided with a handle 24 at its rearward end for effecting linear and/or rotational movement of the inner drive shaft within and with respect to at least one of the outer drive shaft and barrel/support member.

The extended or distal end 18' of the inner drive shaft preferably defines a drive, which may be a hex-shaped screw drive 26 (or other drive shape—e.g., Phillips, straight, and the like), adjacent a flange 28. The hex-shaped drive 26 functions as a "screw driver" tip and is preferably adapted to fit within a correspondingly-shaped mating portion (in this case, a corresponding hex) in a set screw 100 of a spinal fixation system 102 to secure a stabilization rod 104 therein. (See FIG. 7). Flange 28, which is preferably radial/circumferential, may be provided rearwardly adjacent screw drive 26 to prevent the distal end 18' of the inner drive shaft 18 from being pulled into the outer drive shaft 16, thus preventing separation of the two drive shafts.

A pistol grip-type gripping portion 30 may be included, which may extend downwardly, rearward from housing 12 of the screw handling/rod reduction device 10 for convenient holding of the device such that the forward or extended ends of the barrel portion 14 of the device and the drive shafts 16 and 18 may be easily position adjacent a workpiece.

In some of the embodiments of the present invention, the device 10 may include one or more levers associated with corresponding locking (and/or moving) mechanisms for incrementally locking and/or moving the distal end of the outer drive shaft in a forward direction (i.e., away from the housing) and releasing the shaft such that it can be moved rearwardly for reasons which will become apparent.

Preferably, some embodiments include a pair of levers. Such an assembly may include a first lever 32 extending away (e.g., downwardly) from the housing at a angled (e.g., forward) inclination as seen in the figures.

First lever 32 is preferably pivotally mounted on a pin 34 carried by the housing 12 and defines a vertically (relative to the outer drive shaft) extending upper first lever portion 36 defining a pair of parallel walls 38 and 40. In a normal or relaxed mode (non-actuated), rear wall 38 preferably abuts a planar shoulder 42 defined by the housing and the forward upper first lever wall 40 preferably bears against a camber-lock plate 44. Plate 44 preferably defines an aperture therein slightly larger in transverse diameter than the outer diameter of the outer drive shaft 16 such that the plate 44 functions similarly to a conventional camber-lock. Specifically, when plate 44 is oriented perpendicular to the central/longitudinal axis of the outer drive shaft 16, the shaft preferably slides therethrough. If the plate is held in a fixed disposition at an inclination with respect to the axis of the shaft, opposed portions of the plate about the hole thereon preferably abut the shaft and inhibit free sliding movement. While some embodiments of the present invention are illustrated and described with the use of the above-described camber-lock mechanisms, one of skill in the art will appreciate that other locking mechanisms, familiar to those of skill in the art, may be used in place of or in addition to those described.

In the normal or relaxed mode, plate 44 may be in a vertical disposition (relative to the longitudinal "horizontal" axis of the outer drive shaft; see e.g. FIG. 1) when lower inner surface 44a abuts the forward upper first lever wall 40, and also (preferably), when upper rear surface 44b abuts a shoulder 46 defined by the housing of the device. A coil spring 48, or other spring-like or elastic element (e.g., leaf spring, etc.) may be disposed about or adjacent the outer drive shaft 16 and may extend between and bear against the inner surface of camber plate 44 and the rear surface 50' of a rib 50 within the housing 12. Spring 48 thus preferably maintains plate 44 in a perpendicular disposition with respect to the axis of shaft 16 such that the shaft can preferably freely slide therethrough.

Through the aforesaid construction, actuating/squeezing first lever 32 preferably results in the first lever pivoting about pin 34, such that the forward upper first lever wall 40 pushes against the lower portion of the camber plate 44 causing the plate to preferably pivot in a clockwise direction (as seen in the drawings). As plate 44 pivots, the opposed perimeter surfaces disposed about the aperture therein may bear against the surface of the outer drive shaft 16 and force the drive shaft in a first direction (i.e., forwardly). When the first lever is released, plate 44 may be returned to its normal position by coil spring 48, thus retaining the outer drive shaft in a new position. According to some embodiments of the invention, each squeeze of the first lever 32 incrementally advances the outer drive shaft 16.

To prevent the outer drive shaft from simply moving rearwardly, either after the outer drive shaft has been moved by lever 32 or upon the exertion of any rearwardly directed force thereon, a second camber-lock may be provided. The second camber-lock may include a camber plate 51 similar to plate 44. Plate 51 may include an aperture therein adapted to receive the outer drive shaft such that when the plate 51 is normal to the central axis of the drive shaft, the drive shaft may move freely therethrough; however, when plate 51 is inclined slightly in a clockwise direction (as shown in the example illustrated in the drawings), the outer drive shaft may be moved in one direction therethrough (e.g., forwardly) but not in the opposite direction (e.g., rearwardly). A coil spring 52 is disposed about the outer drive shaft 16 between the forward surface 54 of plate 51 and a forward shoulder 56 within the housing 12 of the device to aid in retaining plate 51 in the slight inclined, clockwise position. An abutment pin 58 may be provided in the housing so as to prevent any movement of the lower portion of plate 51 toward the rear of the housing, under the force of spring 52.

A release lever 60, defining a forward upper wall surface 62 and a rear upper wall surface 64, may be included and may be pivotally mounted on a pin 66 in the housing of the device such that pulling rearwardly on the lever 60 preferably results in the forward wall surface 62 of the lever to abut upper rear surface of plate 51 and preferably pivot the plate in a counterclockwise direction about the outer drive shaft. This preferably results in plate 51 being moved from an inclined disposition to a vertical disposition, allowing free sliding movement of the outer drive shaft therethrough (e.g., rearwardly).

In the use of the device 10, according to some embodiments of the present invention, in (for example) installation of a spinal fixation system, device 10 is preferable first loaded with a set screw. This may be accomplished by pushing the handle 24, so that the inner drive shaft 18 is moved forwardly (toward the distal end of barrel 14) such that the screw driver 26 of the inner shaft may protrude through the laterally spaced pusher bars 22 at the distal end of the outer drive shaft 16 (and preferably forwardly of the bifurcated barrel portion 14 of the device). While holding handle 24 in the forward position so as to prevent rearward movement of the inner drive shaft 18, the hexagonal screw drive 26 is pressed into the head of the set screw, attaching the screw to the shaft. Preferably, the mating of the set-screw and drive allows the set-screw to be retained by the drive (via, for example, frictional fit, adhesion, locking action, and the like), such that upon the distal end of the barrel being held in a position lower than the housing, the set-screw does not fall off the end of the drive. Actuating-squeezing the release lever 60 causes counterclockwise rotation of the second camber plate 51 so as to allow the outer drive shaft 16 to move rearwardly.

According to some embodiments, actuating the release lever 60 while pulling rearwardly on the handle 24 results in both the outer and inner drive shafts 16 moving rearwardly. This results in the pulling the set screw attached to the distal end of the inner drive shaft 18 into the bifurcated barrel portion 14 of the device, so as to load the set screw within the device 10. While the device can be used for rod reduction without the preloading of a set screw, the preloading as above described avoids the need to use separate tools (or to then load device 10 with a set screw) to effect rod reduction and securement of the rod via the set screw in the implantation of a spinal fixation system of the type described.

A transverse portion of a stabilization rod can then be disposed between the bifurcated end portions 14a and 14b of the device and positioned over the body member of the pedicle screw. Alignment indicators in the form of protrusions/bumps 68a and 68b may be provided on the distal end of barrel portions 14a and 14b to assist in the alignment of the stabilization protrusions/rods 68c and 68d with corresponding slots 108a (see FIG. 7) in the screw body. With the rod so aligned, actuating/squeezing of the first lever 32 effects clockwise rotation of the camber plate 44 urging the outer drive shaft 16 forwardly. As the outer drive shaft moves forwardly with repeated actuation of first lever 32, the planar ends of end surfaces on the pusher bars contact the stabilization rod and the collar 20 causes the distal ends of bifurcated barrel portions 14a and 14b move inwardly toward each other so as to engage the screw body.

Continued actuation of the first lever preferably causes the pusher bars to urge the stabilization rod into the saddle body member of the pedicle screw. Preferably, the rod is firmly seated but not overly tightened. Thus, continued actuation of the first lever preferably ceases once slight resistance is perceived by the surgeon. In those applications where the body member of the pedicle screw is in a misaligned vertebrae positioned below adjacent vertebra (for example), the gripping of the attached body member of the screw assembly by the end portions of the barrel and the abutment of the pusher bars against the stabilizer rod preferably causes the body member of the screw assembly and the corresponding attached vertebrae to be drawn upwardly to the rod until the rod is seated in the saddle, whereupon the vertebrae will be disposed in a desired alignment.

Once the stabilization rod is firmly seated, the handle 24 may be moved forwardly so as to position the set screw attached to the forward end thereof may be threaded with corresponding threads provided with the body member. While some embodiments of the present invention are illustrated with the use of a set screw which threads internally into the body member of the screw assembly, embodiments of the present invention also may include a set screw which threads onto the external diameter of the body member of the screw assembly. Accordingly, subsequent rotation of the handle 24 in a clockwise direction will seat and threadably engage the set screw in the screw body. Preferably, over torquing is avoided—once tension is detected by the surgeon, rotation of the handle 24 a small amount (in some embodiments, about one turn) in a counterclockwise position generally removes the tension from the locking mechanism such that simultaneous actuation of the release lever and withdrawal of the handle 24 will allow the device 10 to be pulled from the body member of the screw assembly with the stabilization rod and set screw firmly secured to the screw body. Thus, in some embodiments, withdrawal of handle 24 rearwardly, causes collar 22 to move rearwardly, spreading apart the bifurcated end portions, thus releasing the device from the screw assembly.

Figure 7:
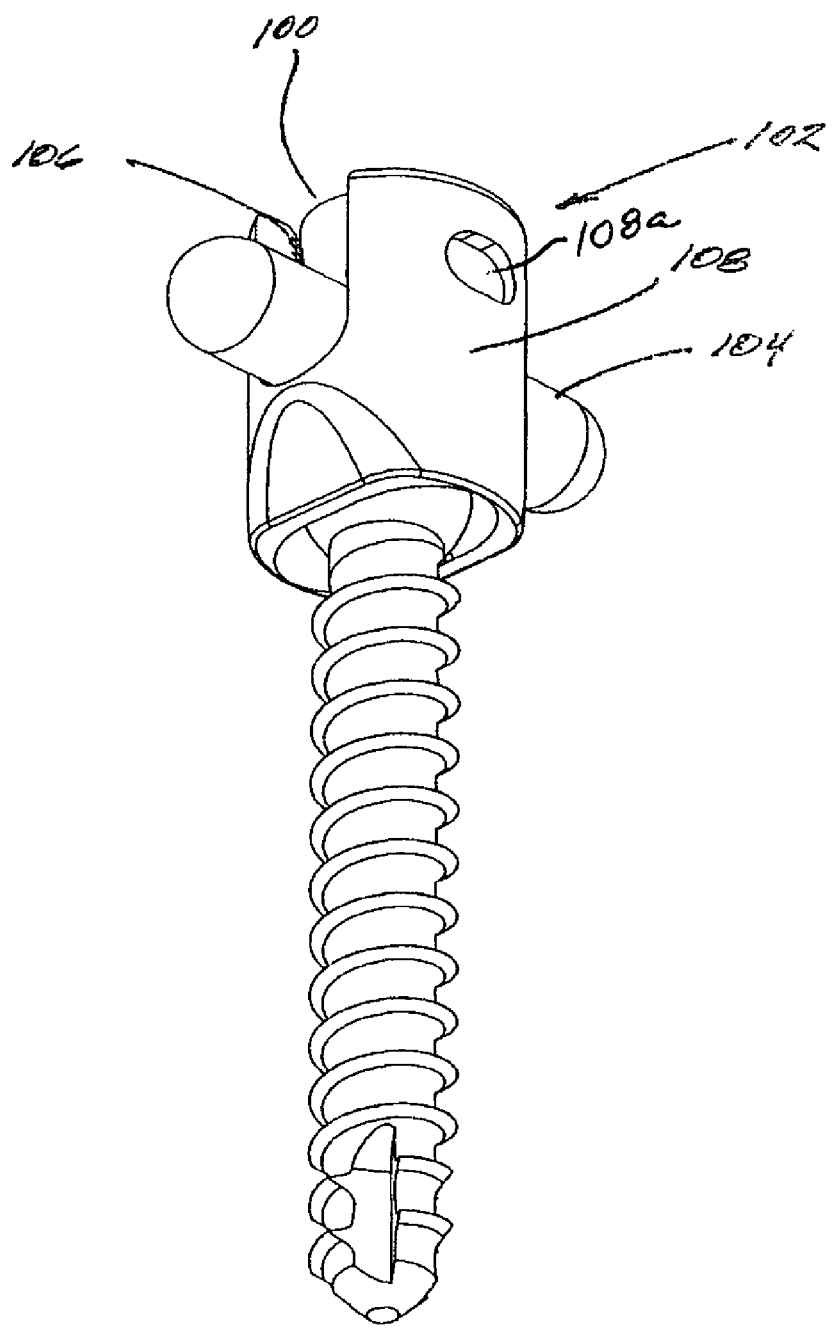
FIG. 7 is schematic of a perspective view of an example of the assembled components of a spinal screw assembly.

An example of an assembled spinal screw assembly is seen in FIG. 7, albeit only a portion of the stabilization rod 104 is illustrated. As seen therein, the rod 104 is disposed within the saddle formed by the opposed slots 106 (only one being shown) in the screw body 108 below the set screw 100.

It is to be understood that while the preferred embodiment of the present invention has been disclosed herein, various minor changes and modifications can be made in carrying out the present invention without departing from the spirit and scope thereof. Such changes and modifications are to be considered as part of the present invention.

I claim:

1. A surgical tool comprising:
    a support member having an end portion and a barrel, said barrel having bifurcated end portions;
    an outer drive shaft capable of movement relative to the barrel;
    an inner drive shaft;
    a drive provided at a forward end of the inner drive shaft;
    a first lever for moving the outer drive shaft in a first direction through the barrel in response to actuation of the first lever;
    a second lever for actuating a release mechanism; and
    an actuator capable of moving the outer drive shaft in a first direction through the support member in response to the actuation of the actuator.

2. The surgical tool according to claim 1, further comprising a collar conveyed by the outer drive shaft along the support member.

3. The surgical tool according to claim 2, wherein the collar includes at least one first protrusion for interaction with a rod of a bone fixation system.

4. The surgical tool according to claim 2, wherein the collar draws the end portions of the barrel together upon movement of the collar in a first direction toward the end portions.

5. The surgical tool according to claim 1, wherein the inner drive shaft is at least one of slidable and rotatable relative to at least one of the support member and outer drive shaft.

6. The surgical tool according to claim 1, further comprising a housing providing adjacent a control end of the tool, wherein the housing includes a gripping portion.

7. The surgical tool according to claim 6, wherein the actuator includes a handle provided adjacent the gripping portion for effecting slidable and/or rotatable movement of the outer drive shaft when the handle is moved relative to the gripping portion.

8. The surgical tool according to claim 1, wherein the drive comprises a screw drive for engaging a corresponding screw recess.

9. The surgical tool according to claim 1, wherein the release second lever further allows for selective directional movement of the outer drive shaft.

10. The surgical tool according to claim 1, wherein the end portion includes a first mating portion for mating with a corresponding second mating portion on a bone anchor of a bone fixation system.

11. The surgical tool according to claim 10, wherein the first mating portion includes a protrusion corresponding to the second mating portion of the bone anchor comprising an opening for receiving the protrusion.

12. The surgical tool according to claim 10, wherein the first mating portion includes a protrusion corresponding to the second mating portion of the bone anchor comprising an opening for receiving the protrusion.

13. The surgical tool according to claim 4, wherein at least one of the bifurcated end portions includes a first mating portion for mating with a corresponding second mating portion on a bone anchor.

14. The surgical tool according to claim 13, wherein the first mating portion includes a protrusion corresponding to the second mating portion of the bone anchor comprising an opening for receiving the protrusion.

15. The surgical tool according to claim 13, wherein the first mating portion includes a recess for receiving the second mating portion comprising of a protrusion.

16. The surgical tool according to claim 1, further comprising a spring.

17. A spinal fixation tool comprising:
    a housing;
    a barrel attached to the housing and defining bifurcated end portions;
    an outer drive shaft slidably mounted on the barrel;
    a collar conveyed by the outer drive shaft for drawing the end portions of the barrel together as the collar is moved thereover;
    an inner drive shaft slidably and rotatably mounted within the outer drive shaft,
    a handle provided adjacent a rearward end of the outer drive shaft for effecting slidable and rotatable movement thereof;
    a screw drive provided on an end of the inner drive shaft for engaging a set screw;
    a first lever for moving the outer drive shaft in a first direction through the barrel in response to actuation of the first lever; and
    a second lever for actuating a release mechanism for selectively allowing movement of the outer drive shaft in a second direction opposite to the first direction.

18. A method for securing a rod within a bone anchor comprising:
    providing a bone fixation tool, the tool comprising a housing, a barrel portion attached to the housing and defining bifurcated end portions, wherein at least one of the end portions includes a first mating portion for mating with a respective mating portion of a bone anchor of a bone fixation system, an outer drive shaft slidably mounted relative to the barrel, a collar attached to an end of the outer driver shaft for drawing the end portions of the barrel together as the collar is moved along the barrel in a first direction toward a distal end of the barrel, an inner drive shaft slidably and rotatably mounted within the outer drive shaft, a screw drive provided on an end of the inner drive shaft for engaging a set screw, a first actuator for moving the outer drive shaft in the first direction through the barrel in response to actuation of the first lever and a second lever for actuating a release mechanism for selectively allowing movement of the outer drive shaft in the second direction;
    moving the inner drive shaft to a position for receiving a set screw;
    loading the screw drive with a set screw;
    actuating the second lever so as to allow movement of the inner and outer drive shaft in the second direction;
    substantially concurrently with actuating the second lever, moving the inner and outer drive shaft in the second direction;
    positioning a transverse section of a bone stabilization rod between the bifurcated end portions;
    positioning the mating portions of the bifurcated end portions adjacent corresponding mating portions of a bone anchor to which the bone stabilization rod will be affixed;
    actuating the first lever at least once so as to urge the outer drive shaft in the first direction so that a portion of the collar contacts the stabilization rod and urges the stabilization rod into a receiving portion of the bone anchor until the stabilization rod is firmly seated within the receiving portion;

moving the inner drive shaft in the first direction so that the set screw is received in corresponding receiving portion on the bone anchor; and rotating inner drive shaft so as to tighten the set screw to the bone anchor.

19. A method for securing a rod within a bone anchor comprising pushing a rod into a recess of body member of a bone anchor assembly using leverage obtained from grasping the bone anchor assembly.

20. The method according to claim 19, further comprising affixing a set screw into the body member while the rod is held in the recess.

* * * * *